US 10,919,886 B2

(12) United States Patent
Sampson et al.

(10) Patent No.: US 10,919,886 B2
(45) Date of Patent: Feb. 16, 2021

(54) SALT AND CRYSTAL FORMS OF PLK-4 INHIBITOR

(71) Applicant: University Health Network, Toronto (CA)

(72) Inventors: Peter Brent Sampson, Oakville (CA); Miklos Feher, New York, NY (US); Heinz W. Pauls, Oakville (CA)

(73) Assignee: UNIVERSITY HEALTH NETWORK, Toronto (CA)

(*) Notice: Subject to any disclaimer, the term of this patent is extended or adjusted under 35 U.S.C. 154(b) by 0 days.

(21) Appl. No.: 16/675,609

(22) Filed: Nov. 6, 2019

(65) Prior Publication Data

US 2020/0140428 A1 May 7, 2020

Related U.S. Application Data

(60) Continuation of application No. 16/389,119, filed on Apr. 19, 2019, now Pat. No. 10,472,353, which is a continuation of application No. 15/886,104, filed on Feb. 1, 2018, now Pat. No. 10,392,374, which is a division of application No. 15/029,373, filed as application No. PCT/CA2014/051001 on Oct. 17, 2014, now Pat. No. 9,884,855.

(60) Provisional application No. 61/892,564, filed on Oct. 18, 2013.

(51) Int. Cl.
   *C07D 413/14* (2006.01)
(52) U.S. Cl.
   CPC ................. *C07D 413/14* (2013.01)
(58) Field of Classification Search
   None
   See application file for complete search history.

(56) References Cited

U.S. PATENT DOCUMENTS

| 7,205,328 | B2 | 4/2007 | He et al. |
| 7,511,059 | B2 | 3/2009 | Schulze et al. |
| 8,263,596 | B2 | 9/2012 | Sampson et al. |
| 8,318,727 | B2 | 11/2012 | Cao et al. |
| 8,481,525 | B2 | 7/2013 | Sampson et al. |
| 8,481,533 | B2 | 7/2013 | Sampson et al. |
| 8,765,748 | B2 | 7/2014 | Pauls et al. |
| 8,921,545 | B2 | 12/2014 | Cumming et al. |
| 8,933,070 | B2 | 1/2015 | Pan et al. |
| 8,999,968 | B2 | 4/2015 | Sampson et al. |
| 9,139,563 | B2 | 9/2015 | Sampson et al. |
| 9,402,828 | B2 | 8/2016 | Pan et al. |
| 9,884,855 | B2 | 2/2018 | Sampson et al. |
| 9,907,800 | B2 | 3/2018 | Sampson et al. |
| 10,358,436 | B2 | 7/2019 | Sampson et al. |
| 10,392,374 | B2 | 8/2019 | Sampson et al. |
| RE47,731 | E | 11/2019 | Sampson et al. |
| 10,472,353 | B2 | 11/2019 | Sampson et al. |

| 2011/0263598 | A1* | 10/2011 | Sampson | C07D 231/56 514/234.5 |
| 2015/0133677 | A1 | 5/2015 | Cumming et al. | |
| 2016/0045511 | A1 | 2/2016 | Sampson et al. | |
| 2016/0250220 | A1 | 9/2016 | Hedley et al. | |
| 2016/0264559 | A1 | 9/2016 | Sampson et al. | |

FOREIGN PATENT DOCUMENTS

| JP | 2008-529985 A | 8/2008 |
| JP | 2010-540463 A | 12/2010 |
| JP | 2011-506494 A | 3/2011 |
| JP | 2012-522729 A | 9/2012 |
| JP | 2012-525345 A | 10/2012 |
| JP | 2014-511336 A | 5/2014 |
| WO | 2007/110559 A1 | 10/2007 |
| WO | 2010/115279 A1 | 10/2010 |

(Continued)

OTHER PUBLICATIONS

U.S. Appl. No. 15/029,373, filed Apr. 14, 2016, U.S. Pat. No. 9,884,855, Issued.
U.S. Appl. No. 15/886,104, filed Feb. 1, 2018, U.S. Pat. No. 10,392,374, Issued.
U.S. Appl. No. 16/389,119, filed Apr. 19, 2019, U.S. Pat. No. 10,472,353, Issued.
Aaltonen et al., Solid form screening—a review. Eur J Pharm Biopharm. Jan. 2009;71(1):23-37.
Ashizawa et al., Polymorphism and crystallization of pharmaceutical drugs. pp. 3-16, Sep. 20, 2002.
Berge et al., Pharmaceutical Salts. Journal of Pharmaceutical Sciences. 1977;66(1):1-19.

(Continued)

*Primary Examiner* — Craig D Ricci
(74) *Attorney, Agent, or Firm* — McCarter & English, LLP; Steven G. Davis; Wei Song

(57) ABSTRACT

A fumarate salt and a maleate salt of compound (I) represented by the following structural formula, as well as their corresponding pharmaceutical compositions, are disclosed. Particular single crystalline forms of 1:1 compound (I) fumarate and 1:1 compound (I) maleate are characterized by a variety of properties and physical measurements. Methods of preparing specific crystalline forms of 1:1 compound (I) fumarate and 1:1 compound (I) maleate are also disclosed. The present invention also provides methods of treating a subject with a cancer.

Compound (I)

22 Claims, 11 Drawing Sheets

(56) References Cited

FOREIGN PATENT DOCUMENTS

| WO | 2010/125004 A1 | 11/2010 |
|---|---|---|
| WO | 2011/123946 A1 | 10/2011 |
| WO | 2011/123947 A1 | 10/2011 |
| WO | 2012/000103 A1 | 1/2012 |
| WO | 2012/048411 A1 | 4/2012 |
| WO | 2012/121764 A1 | 9/2012 |
| WO | 2013/053051 A1 | 4/2013 |
| WO | 2015/054781 A1 | 4/2015 |

OTHER PUBLICATIONS

Brittain, Polymorphism in Pharmaceutical Solids, vol. 95. Marcel Dekker, Inc., New York. 235 pages (1999).

Byrn et al., Pharmaceutical solids: a strategic approach to regulatory considerations. Pharm Res. Jul. 1995;12(7):945-54.

Caira, Crystalline Polymorphism of Organic Compounds. Topics in Current Chemistry, Springer Verlag, Berlin. vol. 198, pp. 163-208 (1998).

CAS RN 1247005-59-9, Spiro[cyclopropane-1,3'-[3H]indol]-2'[1'H]-one, 2-[3-[(1E)-2-[4-[[(2S,6S)-2,6-dimethyl-4-morpholinyl]methyl]phenyl]ethenyl]-1H-indazol-6-yl'-5'-methoxy-, (1R,2S)-(CA Index Name). 1 page, Oct. 26, 2010.

Chouzaigaku: Kiso to Ohyou (Pharmacy: Basics and Application), pp. 142-145, Sep. 20, 1977.

Gu et al., Grouping solvents by statistical analysis of solvent property parameters: implication to polymorph screening. Int J Pharm. Sep. 28, 2004;283(1-2):117-25.

Ivanisevic et al., Uses of X-Ray Powder Diffraction in the Pharmaceutical Industry. Pharmaceutical Sciences Encyclopedia: Drug Discovery, Development, and Manufacturing. John Wiley & Sons, Inc., Shayne C. Gad (Ed.). pp. 1-42, (2010).

Mason et al., Functional characterization of CFI-400945, a Polo-like kinase 4 inhibitor, as a potential anticancer agent. Cancer Cell. Aug. 11, 2014;26(2):163-76.

Morissette et al., High-throughput crystallization: polymorphs, salts, co-crystals and solvates of pharmaceutical solids. Adv Drug Deliv Rev. Feb. 23, 2004;56(3):275-300.

Paulekuhn et al., Trends in active pharmaceutical ingredient salt selection based on analysis of the Orange Book database. J Med Chem. Dec. 27, 2007;50(26):6665-72.

Ribet et al., Conformational analysis and crystal structure of {[1-(3-chloro-4-fluorobenzoyl)-4-fluoropiperidin-4yl]methyl}[(5-methylpyridin-2-yl)methyl]amine, fumaric acid salt. Spectrochim Acta A Mol Biomol Spectrosc. Nov. 2005;62(1-3):353-63.

Sampson et al., The discovery of Polo-like kinase 4 inhibitors: design and optimization of spiro [cyclopropane-1,3?'[3H]indol]-2'(1'H).ones as orally bioavailable antitumor agents. J Med Chem. Jan. 8, 2015;58(1):130-46.

Shin-Seizaigaku (New Pharmaceuticals) pp. 102-103, 232-233, Apr. 25, 1984.

Shin-Yakuzaigaku Souron (New General Review of Pharmaceuticals) p. 111, Apr. 25, 1987.

U.S. Pharmacopeia, X-Ray Diffraction. Chapter 941. Retrieved online at: http://www.pharmacopeia.cn/v29240/usp29nf24s0c941.html. 4 pages (2013).

Zoku-JikkennKagaku Koza (Experimental Chemistry, second series) pp. 159-178, 186-187, Jan. 25, 1967.

Japanese Office Action for Application No. 2016-524077, dated Jul. 5, 2018. 9 pages.

* cited by examiner

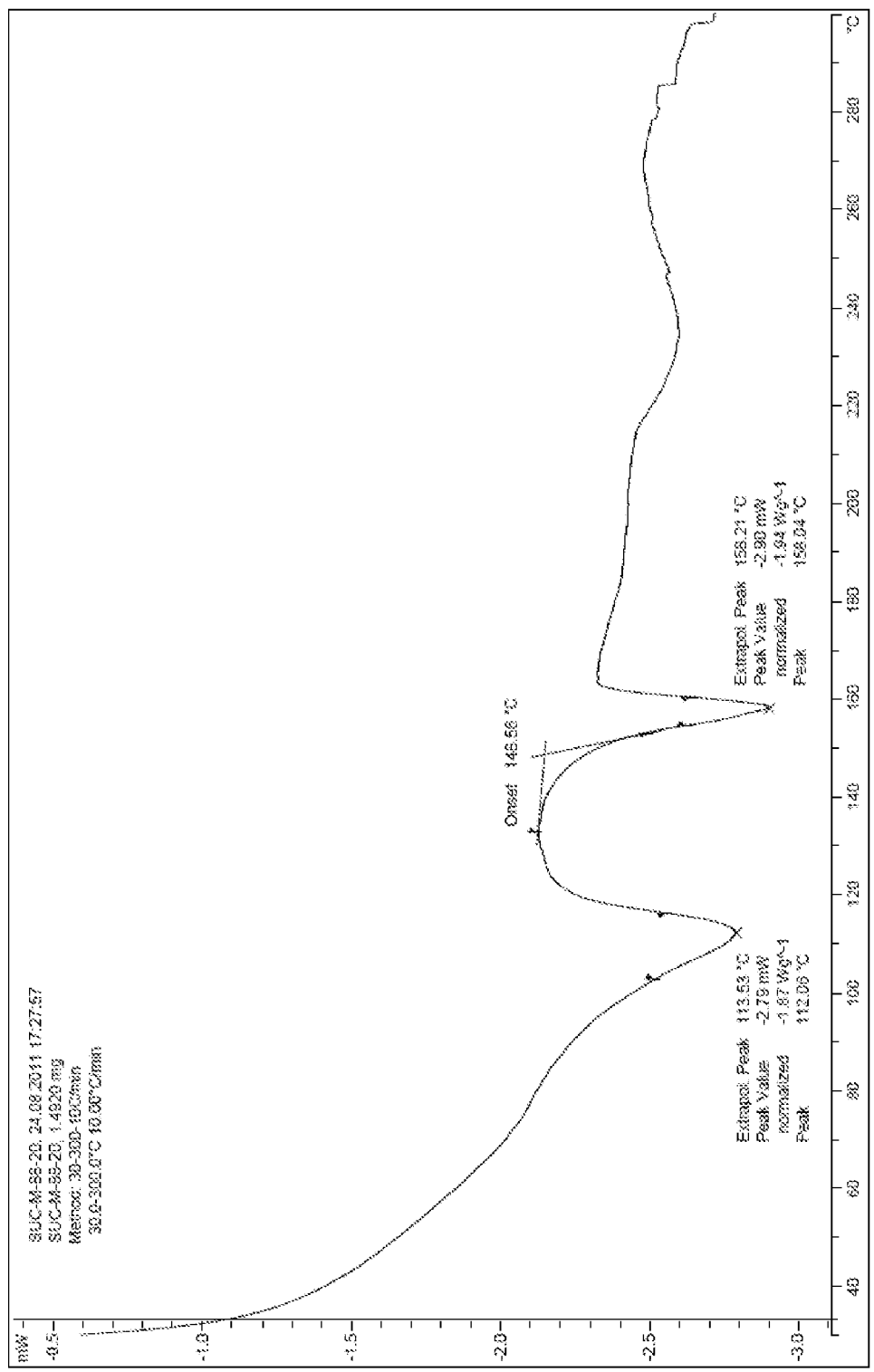
Figure 1. DSC thermogram of (1R,2S)-(E)-2-(3-(4-((cis-2,6-dimethylmorpholino) methyl) styryl)-1H-indazol-6-yl)-5'-methoxyspiro[cyclopropane-1,3'-indolin]-2'-one fumarate form A

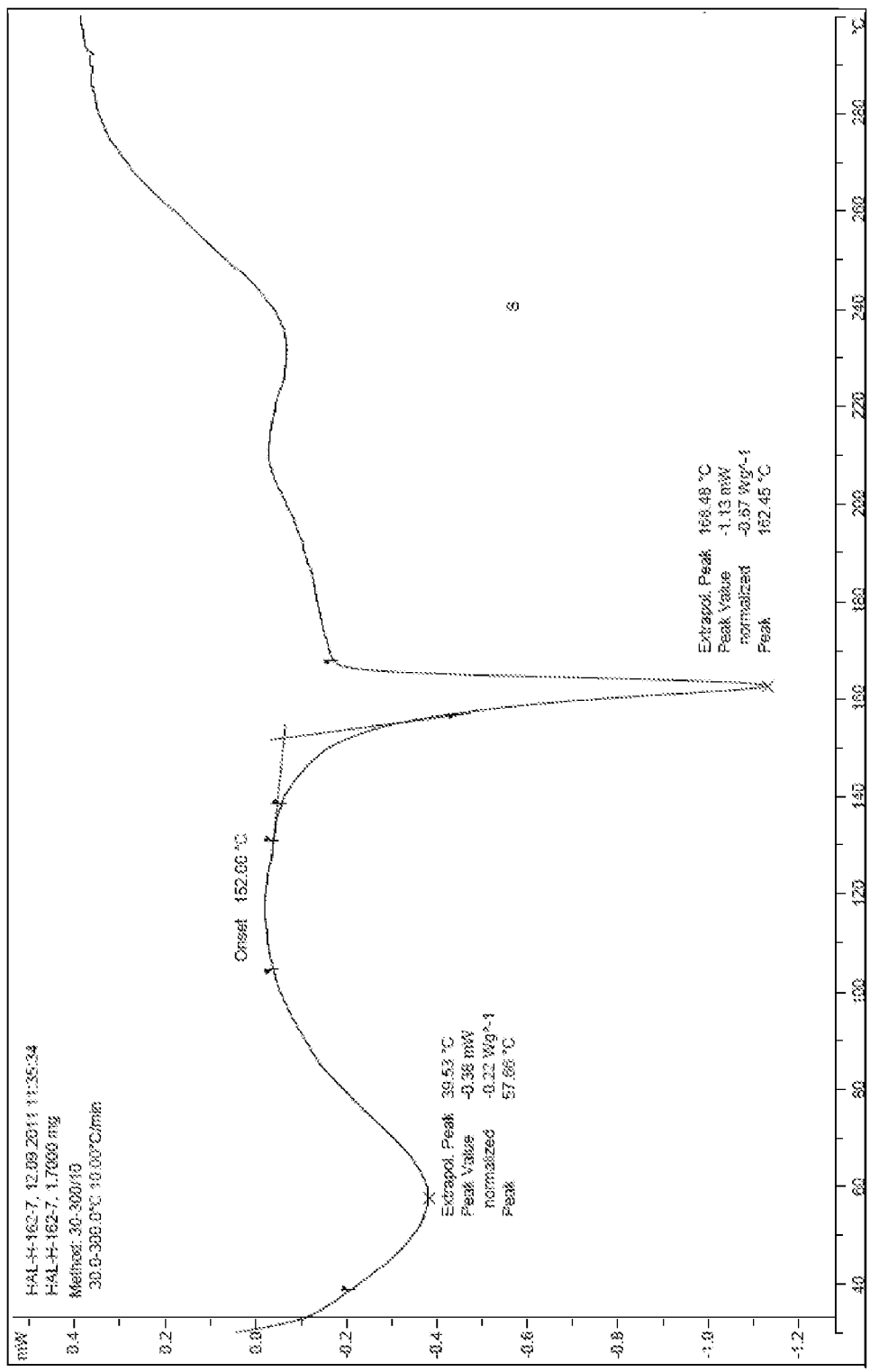
Figure 2. DSC thermogram of (1R,2S)-(E)-2-(3-(4-((cis-2,6-dimethylmorpholino) methyl) styryl)-1H-indazol-6-yl)-5'-methoxyspiro[cyclopropane-1,3'-indolin]-2'-one fumarate form B

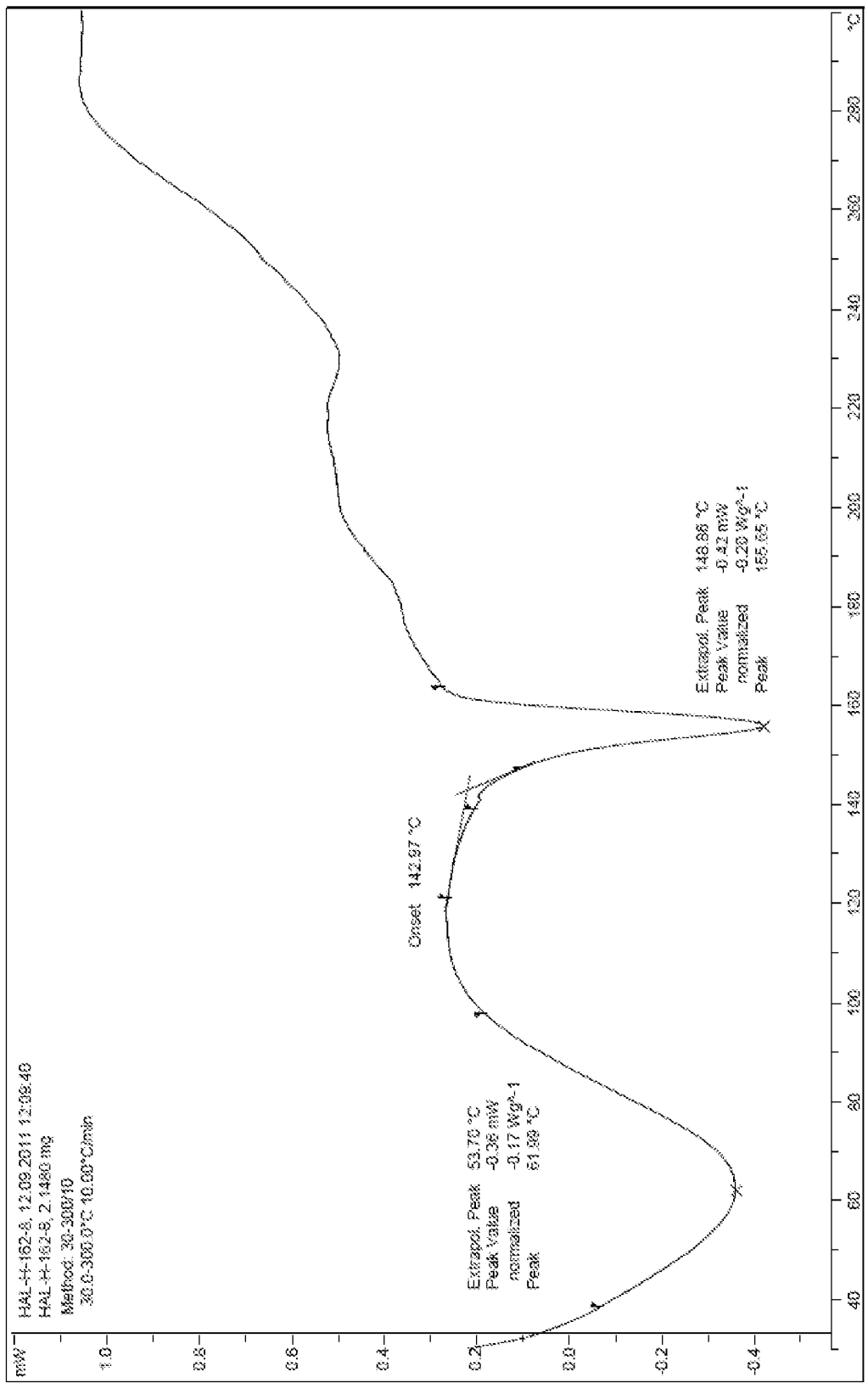
Figure 3. DSC thermogram of (1R,2S)-(E)-2-(3-(4-((cis-2,6-dimethylmorpholino) methyl) styryl)-1H-indazol-6-yl)-5'-methoxyspiro[cyclopropane-1,3'-indolin]-2'-one fumarate form C

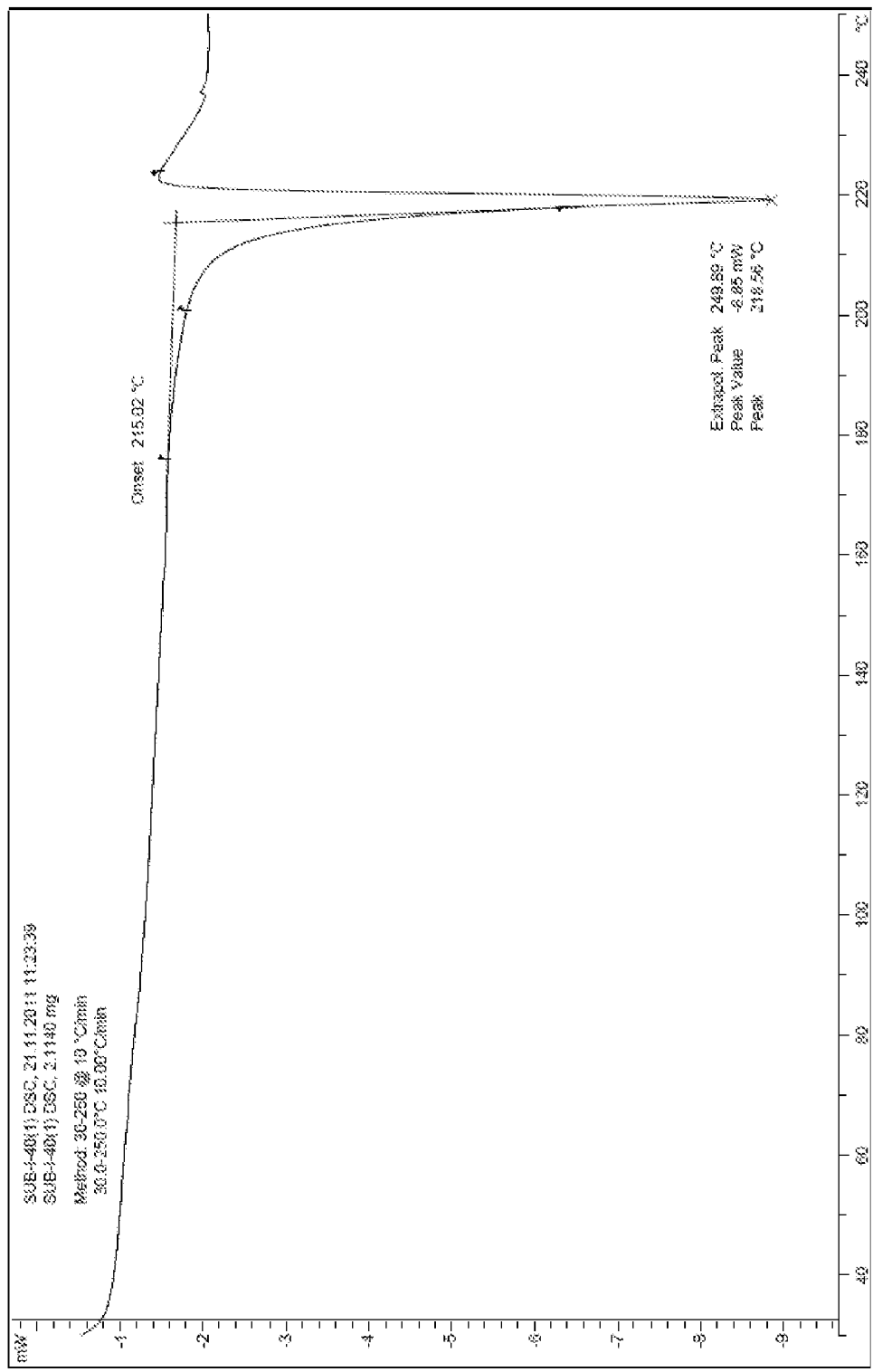
Figure 4. DSC thermogram of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one fumarate form D

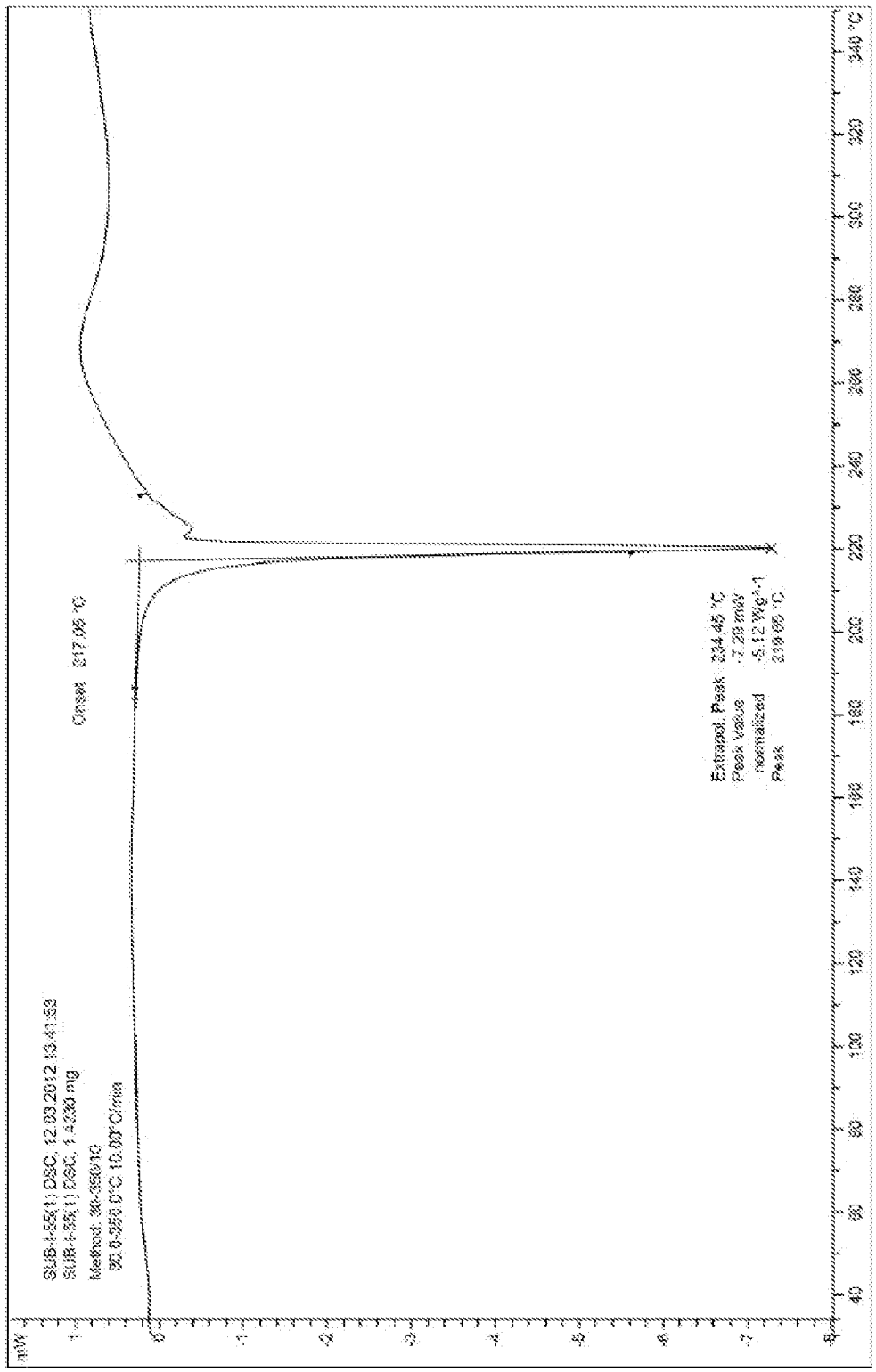
Figure 5. DSC thermogram of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one maleate form A

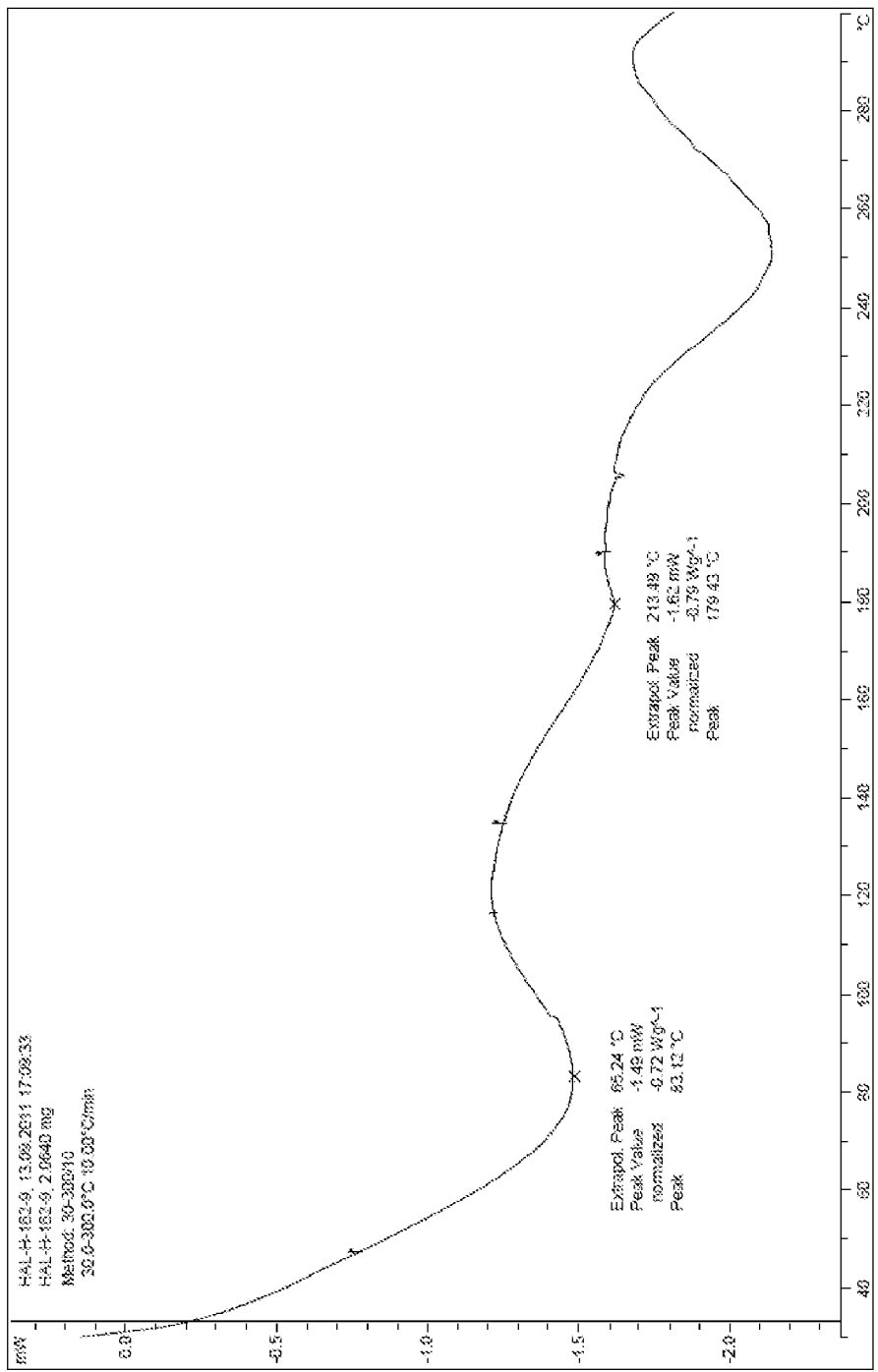
Figure 6. DSC thermogram of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one phosphate Figure 7. XRPD of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one fumarate form A
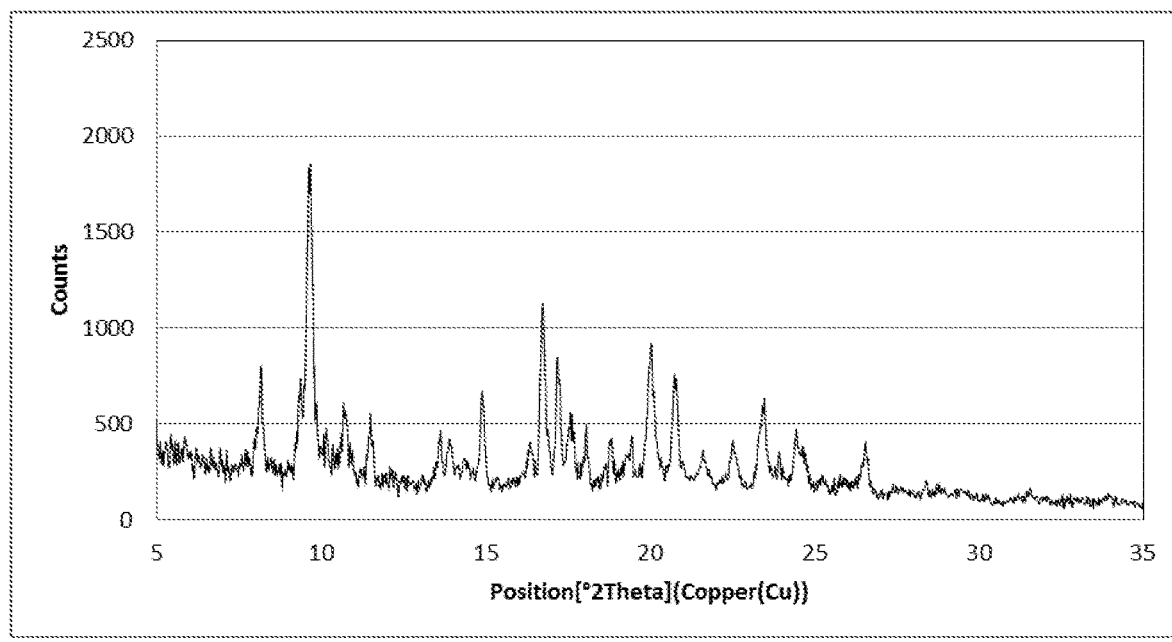

Figure 8. XRPD of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one fumarate form B
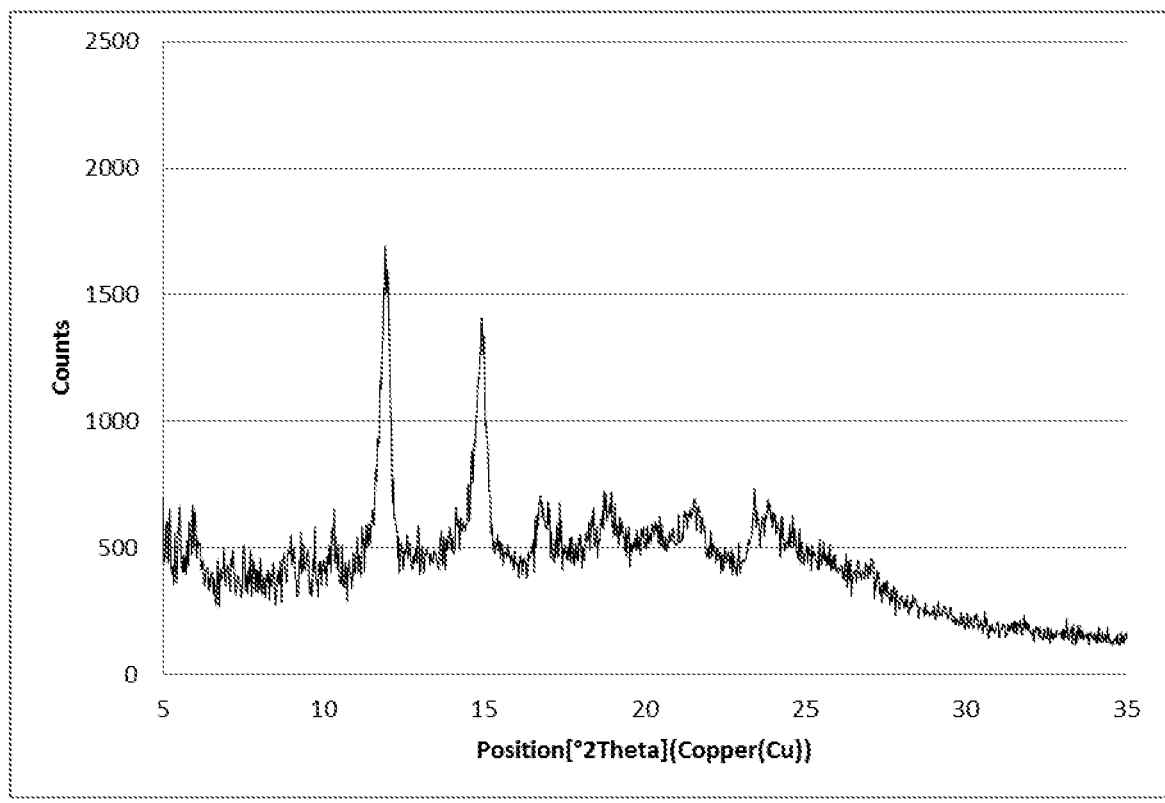

Figure 9. XRPD of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one fumarate form C
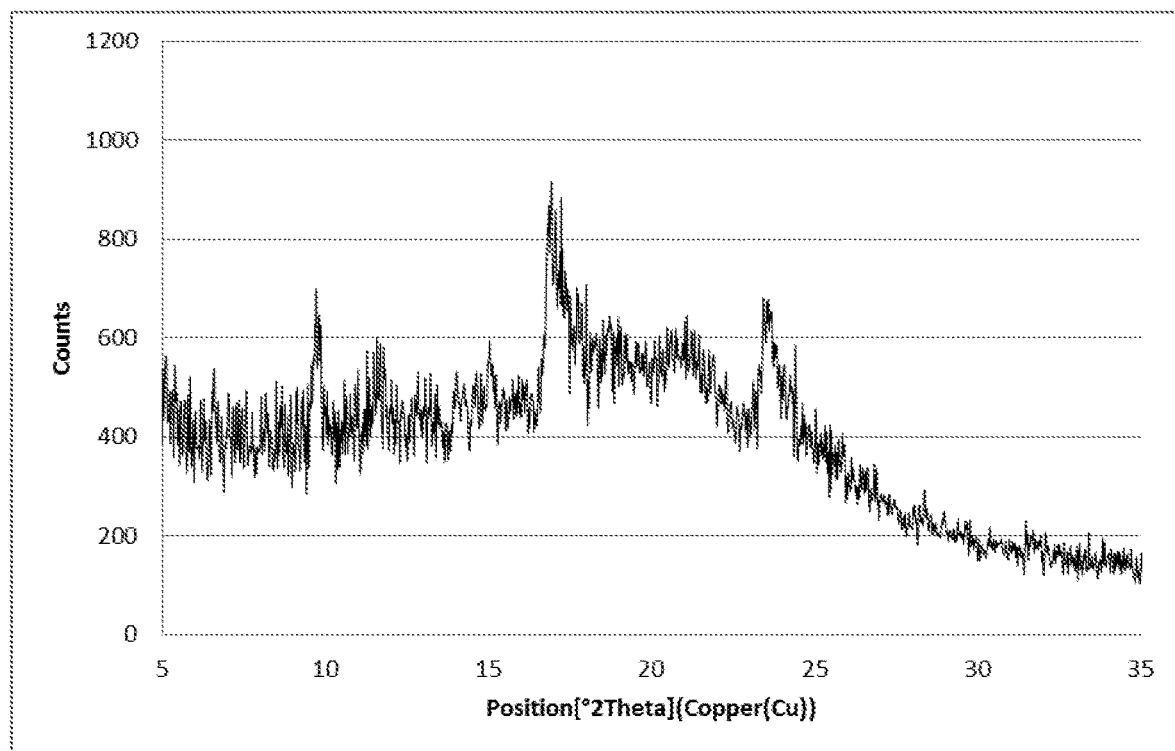

Figure 10. XRPD of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one fumarate form D
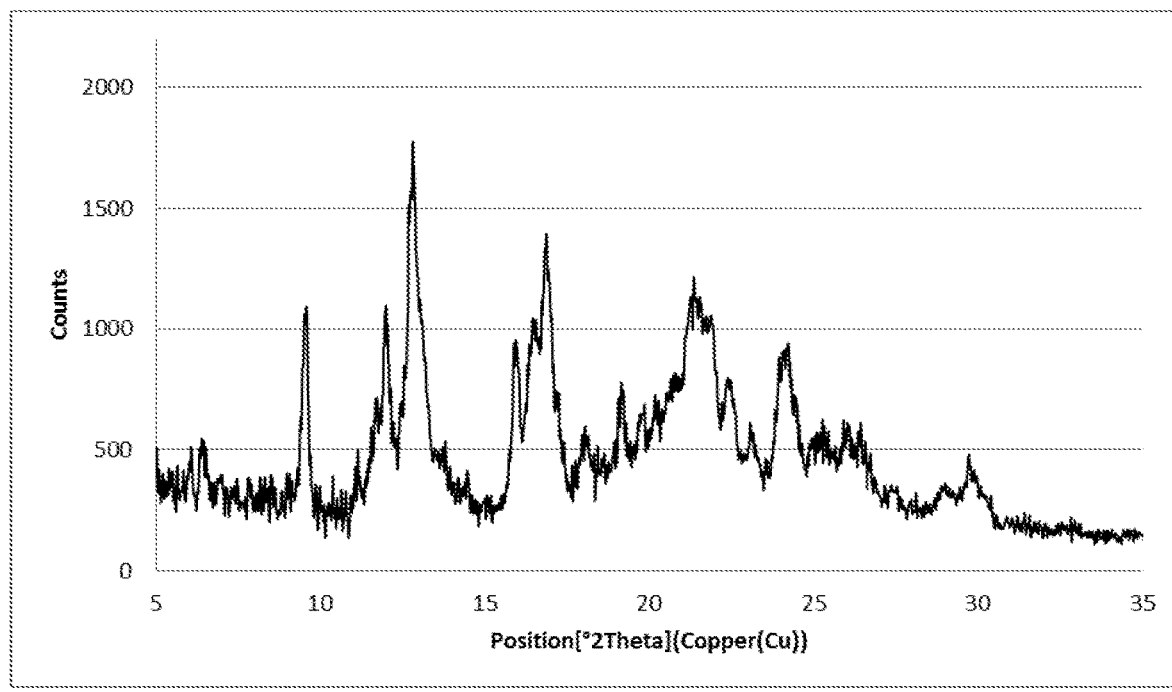

Figure 11. XRPD of (1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one maleate form A
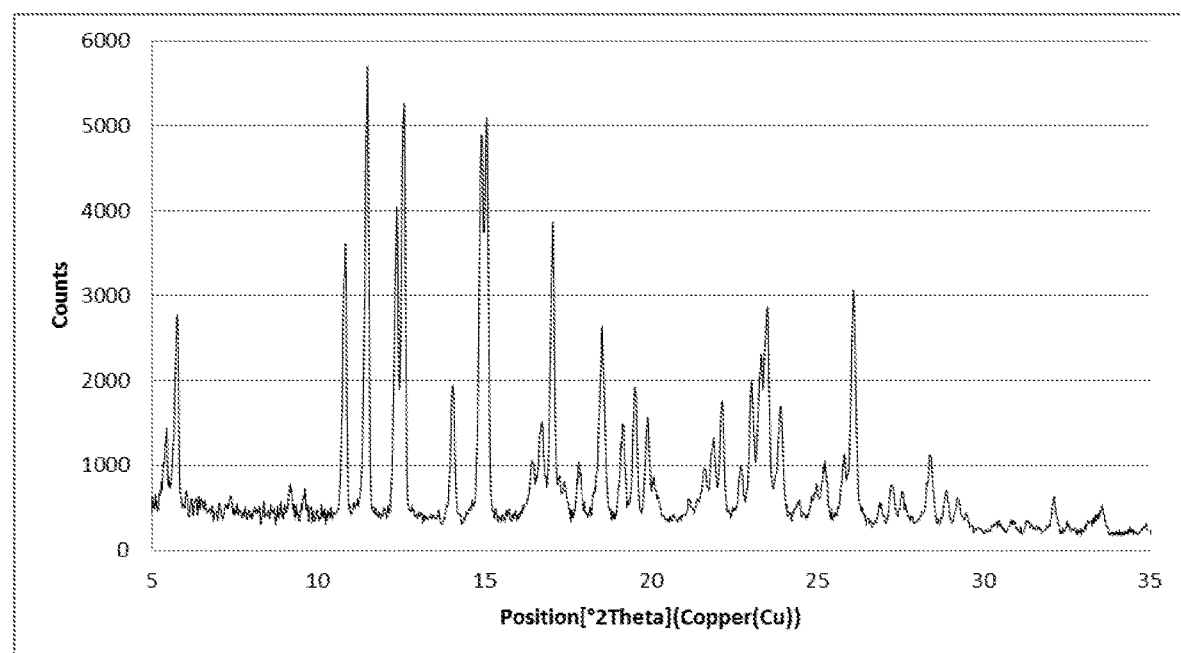

SALT AND CRYSTAL FORMS OF PLK-4 INHIBITOR

RELATED APPLICATIONS

This application is a continuation application of U.S. application Ser. No. 16/389,119, filed Apr. 19, 2019, now U.S. patent Ser. No. 10/472,353, which is a continuation application of U.S. application Ser. No. 15/886,104, filed Feb. 1, 2018, now U.S. Pat. No. 10,392,374, which is a divisional application of U.S. application Ser. No. 15/029,373, filed on Apr. 14, 2016, now U.S. Pat. No. 9,884,855, which is U.S. national stage application of International Application No. PCT/CA2014/051001, filed Oct. 17, 2014, which claims the benefit of U.S. Provisional Application No. 61/892,564, filed Oct. 18, 2013. The entire teachings of each of the aforementioned applications are incorporated herein by reference.

BACKGROUND

The polo-like kinase (PLK) family of serine/threonine kinases comprises at least four known members: PLK1, PLK2 (also known as Snk), PLK3 (also known as Fnk or Prk) and PLK4 (also known as Sak). Agents which inhibit PLK4 have the potential to treat cancer. A number of potent PLK4 inhibitors are disclosed in U.S. Pat. Nos. 8,263,596, 8,481,525, and 8,481,533 (the entire teachings of which are incorporated herein by reference). The structure of one inhibitor disclosed in these patents is shown below as compound (I):

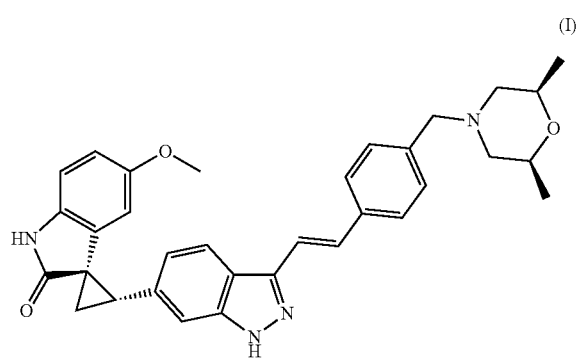 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

(I)

There is a need for salt forms of this compound that are crystalline and otherwise have physical properties that are amenable to large scale manufacture. There is also a need for pharmaceutical formulations in which this drug candidate is stable and is effectively delivered to the patient.

SUMMARY OF THE INVENTION

It has been found that the 1:1 fumaric acid salt and the 1:1 maleic acid salt of compound (I) can be crystallized under well-defined conditions to provide non-hygroscopic crystalline forms. The designation "1:1" is the molar ratio between acid (fumaric or maleic) and compound (I). Because of the two carboxylic acid groups on fumaric acid and maleic acid, it is also possible to form a 1:2 fumaric acid salt and a 1:2 maleic acid salt of compound (I), in which the molar ratio between acid (fumaric or maleic) and compound (I) is 1:2. The 1:1 fumaric acid salt of compound (I) is referred to herein as "1:1 compound (I) fumarate"; and the 1:1 maleic acid salt is referred to herein as "1:1 compound (I) maleate".

1:1 Compound (I) fumarate and 1:1 compound (I) maleate have several advantageous properties when compared with other salts of compound (I). As shown in Examples 1 and 2, many salts of compound (I), including hydrochloride salt, phosphate, sulfate, and citrate, could not be obtained in crystal form. Notably, 1:2 compound (I) fumarate and 1:2 compound (I) maleate also could not be obtained in crystalline form. 1:1 Compound (I) fumarate and 1:1 compound (I) maleate are both non-hygroscopic and easier to formulate than the free base and the other salts. Thus, these favorable properties make 1:1 compound (I) fumarate and 1:1 compound (I) maleate amenable to large scale manufacture and formulation as a drug candidate.

In one aspect, the present invention provides a fumarate salt of compound (I) wherein the molar ratio between compound (I) and fumaric acid is 1:1. As noted above, this salt is also referred to herein as "1:1 compound (I) fumarate".

In another aspect, the present invention provides a maleate salt of compound (I) wherein the molar ratio between compound (I) and maleic acid is 1:1. As noted above, this salt is also referred to herein as "1:1 compound (I) maleate".

In another aspect, the present invention provides a pharmaceutical composition comprising 1:1 compound (I) fumarate (or 1:1 compound (I) maleate) and a pharmaceutically acceptable carrier or diluent.

In still another aspect, the present invention provides a method of treating a subject with cancer, comprising administering to the subject an effective amount of 1:1 compound (I) fumarate or 1:1 compound (I) maleate.

The present invention provides a method of inhibiting PLK4 activity in a subject in need of inhibition of PLK4 activity, comprising administering to the subject an effective amount of 1:1 compound (I) fumarate or 1:1 compound (I) maleate.

The present invention also provides 1:1 compound (I) fumarate or 1:1 compound (I) maleate for use in medicinal therapy. In one embodiment, the medicinal therapy is for treating a subject with cancer. Alternatively, the therapy is for inhibiting PLK4 activity in a subject in need of inhibition of PLK4 activity.

Another aspect of the present invention is the use of 1:1 compound (I) fumarate or 1:1 compound (I) maleate for the manufacture of a medicament for treating a subject with cancer.

Another aspect of the present invention is 1:1 compound (I) fumarate or 1:1 compound (I) maleate for treating a subject with cancer.

Another aspect of the present invention is the use of a 1:1 compound (I) fumarate or 1:1 compound (I) maleate for the manufacture of a medicament for inhibiting PLK4 activity in a subject in need of inhibition of PLK4 activity.

Another aspect of the present invention is 1:1 compound (I) fumarate or 1:1 compound (I) maleate for inhibiting PLK4 activity in a subject in need of inhibition of PLK4 activity.

BRIEF DESCRIPTION OF THE DRAWINGS

FIG. 1 shows the Differential Scanning calorimetry Analysis (DSC) thermogram for form A of 1:1 compound (I) fumarate.

FIG. 2 shows the DSC thermogram for form B of 1:1 compound (I) fumarate.

FIG. 3 shows the DSC thermogram for form C of 1:1 compound (I) fumarate.

FIG. 4 shows the DSC thermogram for form D of 1:1 compound (I) fumarate.

FIG. 5 shows the DSC thermogram for form A of 1:1 compound (I) maleate.

FIG. 6 shows the DSC thermogram for phosphate of compound (I).

FIG. 7 shows the X-ray Powder Diffraction (XRPD) pattern for form A of 1:1 compound (I) fumarate.

FIG. 8 shows the XRPD pattern for form B of 1:1 compound (I) fumarate.

FIG. 9 shows the XRPD pattern for form C of 1:1 compound (I) fumarate.

FIG. 10 shows the XRPD pattern for form D of 1:1 compound (I) fumarate.

FIG. 11 shows the XRPD pattern for form A of 1:1 compound (I) maleate.

DETAILED DESCRIPTION OF THE INVENTION

The present invention provides 1:1 compound (I) fumarate, 1:1 compound (I) maleate, unique crystalline forms thereof and their corresponding pharmaceutical compositions. The present invention also provides methods of treating a subject with a cancer. Additionally, the present invention provides methods for preparing specific crystalline forms of 1:1 compound (I) fumarate and 1:1 compound (I) maleate.

Crystalline Forms of 1:1 Compound (I) Fumarate and 1:1 Compound (I) Maleate

In a particular embodiment, at least a particular percentage by weight of 1:1 compound (I) fumarate or 1:1 compound (I) maleate is crystalline. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100%. For example, in one embodiment, at least 80% (e.g., at least 90% or 99%) by weight of the 1:1 compound (I) fumarate or the 1:1 compound (I) maleate is crystalline. It is to be understood that all values and ranges between these values and ranges are meant to be encompassed by the present invention.

In another particular embodiment, at least a particular percentage by weight of 1:1 compound (I) fumarate and 1:1 compound (I) maleate is a single crystalline form. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100%. For example, in one embodiment, at least 80% (e.g., at least 90% or 99%) by weight of the 1:1 compound (I) fumarate and 1:1 compound (I) maleate is in a single crystalline form. It is to be understood that all values and ranges between these values and ranges are meant to be encompassed by the present invention.

As used herein, "crystalline" refers to a solid having a crystal structure wherein the individual molecules have a highly homogeneous regular locked-in chemical configuration. Crystalline 1:1 compound (I) fumarate and crystalline 1:1 compound (I) maleate can be crystals of a single crystalline form of 1:1 compound (I) fumarate and 1:1 compound (I) maleate, or a mixture of crystals of different single crystalline forms. A single crystalline form means 1:1 compound (I) fumarate or 1:1 compound (I) maleate as a single crystal or a plurality of crystals in which each crystal has the same crystal form.

When a particular percentage by weight of 1:1 compound (I) fumarate (or 1:1 compound (I) maleate) is a single crystalline form, the remainder of the fumarate (or 1:1 compound (I) maleate) is some combination of amorphous fumarate (or 1:1 compound (I) maleate), and/or one or more other crystalline forms of 1:1 compound (I) fumarate (or 1:1 compound (I) maleate) excluding the single crystalline form. When the crystalline 1:1 compound (I) fumarate (or crystalline 1:1 compound (I) maleate) is defined as a specified percentage of one particular crystalline form of 1:1 compound (I) fumarate (or 1:1 compound (I) maleate), the remainder is made up of amorphous form and/or crystalline forms other than the one or more particular forms that are specified. Examples of a single crystalline form include form A of 1:1 compound (I) fumarate (or 1:1 compound (I) maleate) characterized by one or more properties as discussed herein.

1:1 Compound (I) fumarate (or 1:1 compound (I) maleate) is at least 60%, 70%, 80%, 90%, 99% or 99.9% by weight pure relative to the other stereoisomers, i.e., the ratio of the weight of the stereoisomer over the weight of all the stereoisomers.

Preparation of Crystalline Forms of 1:1 Compound (I) Fumarate and 1:1 Compound (I) Maleate The particular solid forms of 1:1 compound (I) fumarate or 1:1 compound (I) maleate can be prepared, for example, by slow evaporation, slow cooling, and antisolvent precipitation.

As used herein, "anti-solvent" refers to a solvent, in which 1:1 compound (I) fumarate or 1:1 compound (I) maleate has low solubility and cause the fumarate or maleate to precipitate out of solution in the form of fine powder or crystals.

Alternatively, 1:1 compound (I) fumarate or 1:1 compound (I) maleate can then be recrystallized from a suitable solvent with or without the addition of a seed crystal.

The preparation of each specific solid forms of 1:1 compound (I) fumarate or 1:1 compound (I) maleate is described in the experimental section below.

Characterization of Crystalline Forms of 1:1 Compound (I) Fumarate and 1:1 Compound (I) Maleate Samples are irradiated with copper K-alpha X-rays with the X-ray tube operated at 40 kV/30 mA. In one embodiment, 1:1 compound (I) fumarate is a single crystalline form, form A. In a specific embodiment, form A of 1:1 compound (I) fumarate is characterized by the X-ray powder diffraction pattern shown in FIG. 7. In a more particular embodiment, 1:1 compound (I) fumarate form A is characterized by an X-ray powder diffraction pattern which comprises peaks (2θ angles) at:

a) 9.7°, 16.7°, and 20.1°±0.2 in 2θ (major peaks); or
b) 8.2°, 9.7°, 16.7°, and 20.1°±0.2 in 2θ; or
c) 8.2°, 9.7°, 10.7°, 11.5°, 14.9°, 16.7°, 20.1°, and 23.5°±0.2 in 2θ; or
d) 8.2°, 9.7°, 10.7°, 11.5°, 13.6°, 14.9°, 16.7°, 18.1°, 18.8°, 20.1°, 23.5°, and 24.5°±0.2 in 2θ.

The major peaks described herein have a relative intensity over 50% in form A. It is to be understood that a specified 2θ angle means the specified value ±0.2°.

In another specific embodiment, 1:1 compound (I) fumarate form A is characterized by differential scanning calorimeter (DSC) peak phase transition temperatures of 112° C. and 158° C.

In another embodiment, 1:1 compound (I) fumarate is a single crystalline form, form B. In a specific embodiment, form B of 1:1 compound (I) fumarate is characterized by the X-ray powder diffraction pattern shown in FIG. 8. In a more particular embodiment, 1:1 compound (I) fumarate form B is characterized by an X-ray powder diffraction pattern which comprises peaks at:

a) 11.9° and 14.9°±0.2 in 2θ (major peaks); or
b) 11.9°, 14.9°, 18.7°, and 21.5°±0.2 in 2θ; or
c) 5.5°, 5.9°, 11.9°, 14.9°, 16.7°, 17.4°, 18.7°, 21.5°, and 23.4°±0.2 in 2θ.

The major peaks described herein have a relative intensity over 75% in form B.

In another specific embodiment, 1:1 compound (I) fumarate form B is characterized by differential scanning calorimeter (DSC) peak phase transition temperatures of 58° C. and 162° C.

In another embodiment, 1:1 compound (I) fumarate is a single crystalline form, form C. In a specific embodiment, 1:1 compound (I) fumarate form C is characterized by the X-ray powder diffraction pattern of the single crystalline shown in FIG. 9. In a more particular embodiment, 1:1 compound (I) fumarate form C is characterized by an X-ray powder diffraction pattern which comprises peaks at:

a) 16.8°, 16.9°, and 19.9°±0.2 in 2θ (major peaks); or
b) 9.8°, 16.8°, 16.9°, 19.9°, and 23.5°±0.2 in 2θ; or
c) 9.7°, 9.8°, 11.7°, 15.1°, 16.8°, 16.9°, 19.9°, 23.5°, and 23.7°±0.2 in 2θ.

The major peaks described herein have a relative intensity over 75% in form C.

In another specific embodiment, 1:1 compound (I) fumarate form C is characterized by differential scanning calorimeter (DSC) peak phase transition temperatures of 62° C. and 156° C.

In another embodiment, 1:1 compound (I) fumarate is a single crystalline form, form D. In a specific embodiment, Form D of 1:1 compound (I) fumarate is characterized by the X-ray powder diffraction pattern in FIG. 10. In a more specific embodiment, the X-ray diffraction pattern of Form D comprises peaks at:

a) 9.6°, 12.8°, 16.0°, and 22.0°±0.2 in 2θ (major peaks); or
b) 9.6°, 12.8°, 16.0°, 16.9°, 21.2°, and 22.0°±0.2 in 2θ; or
c) 9.6°, 12.8°, 16.0°, 16.9°, 20.8°, 21.2°, 21.5°, and 22.0°±0.2 in 2θ.
d) 9.6°, 11.7°, 12.0°, 12.8°, 16.0°, 16.6°, 16.9°, 18.1°, 19.2°, 19.8°, 20.7°, 20.8°, 21.2°, 21.5°, 22.0°, 22.5°, 24.0°, 26.0°, and 29.8°±0.2 in 2θ.

The major peaks described herein have a relative intensity over 85% in form D.

In another specific embodiment, at least 90% by weight of the 1:1 compound (I) fumarate Form D is characterized by differential scanning calorimeter (DSC) peak phase transition temperature of 219° C.

In another embodiment, 1:1 compound (I) maleate is a single crystalline form, Form A. In a specific embodiment, form A of 1:1 compound (I) maleate is characterized by the X-ray powder diffraction pattern in FIG. 11. In a more specific embodiment, form A of 1:1 compound (I) maleate is characterized by the X-ray powder diffraction pattern which comprises peaks at:

a) 11.5°, 12.6°, 14.9°, and 15.1°±0.2 in 2θ; or
b) 10.8°, 11.5°, 12.4°, 12.6°, 14.9°, 15.1°, and 17.1°±0.2 in 2θ; or
c) 5.8°, 10.8°, 11.5°, 12.4°, 12.6°, 14.9°, 15.1°, 17.1°, 18.6°, 23.5°, and 26.1°±0.2 in 2θ; or
d) 5.5°, 5.8°, 10.8°, 11.5°, 12.4°, 12.6°, 14.1°, 14.9°, 15.1°, 16.7°, 17.1°, 17.8°, 18.6°, 19.5°, 19.9°, 21.9°, 22.2°, 23.0°, 23.3°, 23.5°, 23.9°, and 26.1°±0.2 in 2θ.

The major peaks described herein have a relative intensity over 90% in form A.

In another specific embodiment, 1:1 compound (I) maleate form A is characterized by differential scanning calorimeter (DSC) peak phase transition temperature of 219° C.

The fumarate salt of compound (I) or the maleate salt of compound (I) described herein is either in an amorphous form or in a crystalline form. The fumarate salt of compound (I) or the maleate salt of compound (I) described in the present invention includes both an unsolvated form and a solvate form.

"Solvate form" refers to a solid or a crystalline form of the fumarate salt of compound (I) or the maleate salt of compound (I), where solvent is combined with the fumarate salt of compound (I) or the maleate salt of compound (I) in a definite ratio (e.g., a molar ratio of 1:1 or 1:2) as an integral part of the solid or a crystal.

"Unsolvated form" refers to no definite ratio between a solvent molecule and the fumarate salt of compound (I) or the maleate salt of compound (I), and the solvent molecule is not substantially (e.g., less that 10% by weight) existed in the fumarate salt of compound (I) or the maleate salt of compound (I). Well known solvent molecules include water, methanol, ethanol, n-propanol, and isopropanol.

In the present invention, form A of 1:1 compound (I) fumarate is an isopropanol solvate, which has a molar ratio of 2:1 between the compound (I) fumarate and isopropanol. Form B-D of 1:1 compound (I) fumarate and form A of 1:1 compound (I) maleate described herein are not solvates, i.e., each are an unsolvated form.

Methods of Treatment Using Compound (I) Fumarate and Compound (I) Maleate

1:1 Compound (I) fumarate and 1:1 compound (I) maleate can inhibit various kinases, including PLK4. Thus, 1:1 compound (I) fumarate and 1:1 compound (I) maleate of the invention are useful in the treatment of diseases or conditions associated with such kinase. For example, PLK4 is believed to be involved in cellular mitotic progression. Thus, small molecule inhibitors of this enzyme can be potential anti-tumor agents.

In a specific embodiment, 1:1 compound (I) fumarate and 1:1 compound (I) maleate are PLK4 inhibitors, and are useful for treating diseases, such as cancer, associated with such a kinase.

Another aspect of the invention relates to a method of treating a subject with cancer, comprising administering to the subject an effective amount of 1:1 compound (I) fumarate and 1:1 compound (I) maleate. In one embodiment, 1:1 compound (I) fumarate and 1:1 compound (I) maleate inhibit the growth of a tumor. Specifically, 1:1 compound (I) fumarate and 1:1 compound (I) maleate inhibit the growth of a tumor that overexpresses PLK4. In another embodiment, 1:1 compound (I) fumarate and 1:1 compound (I) maleate inhibit the growth of the tumor by inducing apoptosis of the tumor cells or by inhibiting proliferation of the tumor cells.

Cancers that can be treated or prevented by the methods of the present invention include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one specific embodiment, the cancer is lung cancer, breast cancer, colon cancer, neuroblastoma, prostate cancer, melanoma, glioblastoma multiforme, ovarian cancer, lymphoma, leukemia, osteosarcoma, germinoma, glioma, fibrosarcoma, gastrointestinal sarcoma, fibrous histiocytoma, round cell sarcoma, synovial sarcoma, cervical cancer, anogenital cancer, head and neck cancer, and oropharyngeal cancer. In one specific embodiment, the cancer is lung cancer, colon cancer, brain cancer, neuroblastoma, prostate cancer, melanoma, glioblastoma multiforme or ovarian cancer. In another specific embodiment, the cancer is lung cancer, breast cancer, colon cancer, brain cancer, neuroblastoma, prostate cancer, melanoma, glioblastoma multiform or ovarian cancer. In another specific embodiment, the cancer is lung cancer, breast cancer, and colon cancer. In yet another specific embodiment, the cancer is a breast cancer. In yet another specific embodiment, the cancer is a basal sub-type breast cancer or a luminal B sub-type breast cancer. In one embodiment, the basal sub-type breast cancer is ER (estrogen receptor), HER2 and PR (progesterone receptor) negative breast cancer. In yet another specific embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

The invention further relates to a method of treating a subject with tumor cells, comprising administering to the subject, an amount of a compound disclosed herein that is effective to reduce effectively PLK4 activity in the subject.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

As used herein, "treating a subject with a cancer" includes achieving, partially or substantially, one or more of the following: arresting the growth of a cancer, reducing the extent of a cancer (e.g., reducing size of a tumor), inhibiting the growth rate of a cancer, ameliorating or improving a clinical symptom or indicator associated with the cancer (such as tissue or serum components) or increasing longevity of the subject; and reducing the likelihood of recurrence of the cancer.

As used herein, the term "reducing the likelihood of recurrence of a cancer" means inhibiting or delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

Generally, an effective amount of a compound of the invention varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present invention may be readily determined by one of ordinary skill by routine methods known in the art.

In an embodiment, an effective amount of 1:1 compound (I) fumarate and 1:1 compound (I) maleate ranges from about 0.01 to about 1000 mg/kg body weight, alternatively about 0.05 to about 500 mg/kg body weight, alternatively about 0.1 to about 100 mg/kg body weight, alternatively about 0.1 to about 15 mg/kg body weight, alternatively about 1 to about 5 mg/kg body weight, and in another alternative, from about 2 to about 3 mg/kg body weight. The skilled artisan will appreciate that certain factors may influence the dosage required to effectively treat a subject suffering from cancer and these factors include, but are not limited to, the severity of the disease or disorder, previous treatments, the general health and/or age of the subject and other diseases present.

Moreover, a "treatment" regime of a subject with an effective amount of the compound of the present invention may consist of a single administration, or alternatively comprise a series of applications. For example, 1:1 compound (I) fumarate and 1:1 compound (I) maleate may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds of the invention can be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Pharmaceutical Compositions Including 1:1 Compound (I) Fumarate and 1:1 Compound (I) Maleate 1:1 Compound (I) fumarate or 1:1 compound (I) maleate or any one or more of the crystal forms disclosed herein can be suitably formulated into pharmaceutical compositions for administration to a subject.

In one embodiment, the present invention provides a pharmaceutical composition comprising 1:1 Compound (I) fumarate or 1:1 compound (I) maleate as described above, and a pharmaceutically acceptable carrier or diluent, wherein at least 80% (preferably 90%, more preferably 99%) by weight of the salt is crystalline.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The invention is illustrated by the following examples, which are not intended to be limiting in any way.

EXPERIMENTAL

Abbreviations

BSA benzene sulfonic acid
d days
EtOAc ethyl acetate
EtOH ethanol
h hours
HPLC high performance liquid chromatography
IPA isopropanol
IBAc isobutyl acetate
MeOH methanol
MIBK methyl isobutyl ketone
min minutes
MTBE methyl tert-butylether
NMR nuclear magnetic resonance
pTSA para toluenesulfonic acid
RBF round bottom flask
RH relative humidity
Rel. Int. relative intensity
rt room temperature
temp temperature
TGA thermogravimetric analysis
THF tetrahydrofuran
wt % percent by weight
XRPD X-ray powder diffraction Analysis Conditions Differential Scanning Calorimetry Analysis (DSC)

DSC analyses were carried out on a Mettler 822e differential scanning calorimeter or a TA instruments Q2000. Samples were weighed in an aluminum pan, covered with a pierced lid, and then crimped. Analysis conditions were 30-120, 30-200, 30-300° C. and 40-300° C. ramped at 10° C./min.

Thermal Gravimetric Analysis (TGA)

TGA analyses were carried out on a Mettler 851e SDTA thermogravimetric analyzer. Samples were weighed in an alumina crucible and analyzed from 30-230, 30-300 and 30-350° C. and at a ramp rate of 10° C./min.

X-Ray Powder Diffraction (XRPD)

Samples were analyzed on a Panalytical CubiX-Pro X-ray powder diffractometer or a Bruker AXS/Siemens D5000 diffractometer.

Panalytical Conditions: Samples were placed on a silicon zero-return ultra-micro sample holder. The samples were irradiated with copper K-alpha X-rays with the X-ray tube operated at 40 kV/30 mA. The samples were scanned in continuous mode along the range 3 to 45°.

Bruker AXS/Siemens D5000 Conditions: A high-power Cu-target was used operating at 50 kV/35 mA. The secondary beam was monochromatized by a solid state Kevex detector. The samples were scanned along the range 2-35° (2σ) where representative peaks for most of the organic crystalline compounds occur.

Gravimetric Moisture Sorption

Gravimetric moisture sorption experiments were carried out on a Hiden dynamic vapour sorption analyzer by first holding the sample at 40% RH and 25° C. until an equilibrium weight was reached or for a maximum of four hours. The sample was then subjected to an isothermal (25° C.) adsorption scan from 40 to 90% RH in steps of 10%. The sample was allowed to equilibrate to an asymptotic weight at each point for a maximum of four hours. Following adsorption, a desorption scan from 85 to 5% RH (at 25° C.) was run in steps of −10% again allowing a maximum of four hours for equilibration to an asymptotic weight. An adsorption scan was then performed from 0% RH to 40% RH in steps of +10% RH.

Raman Spectroscopy

Samples for Raman analysis were analyzed on a Kaiser RXN1 Macroscope with PhAT Probe. Solids obtained from the 96 well plate crystallizations were analyzed using the following conditions:

Raman Source: 785 nm laser
Microscope Objective 1.2 mm
Single Exposure Time: 12 sec
Co-additions: 12
Enabled Exposure options: Cosmic Ray filtering, Dark Subtraction, Intensity Calibration Optical Microscopy Samples were examined with a Leica DMRB polarized light microscope combined with a digital camera (1600× 1200 resolution). Small amounts of samples were dispersed in mineral oil on a glass slide with cover slips and viewed with 100× magnification or higher.

Birefringence

Samples for Birefringence analysis were analyzed on a Coleman Technologies birefringence imager. Solids obtained from the 96 well plate crystallizations were analyzed using the following conditions:

Lighting: 37
Exposure: 57.9
Polarization: 0.0
Well mask diameter: 6.2
Target Intensity: 80
Target Percentile: 90.0
Maximum Mean Intensity: 100

Nuclear Magnetic Resonance

Samples for Proton NMR were analyzed using a Bruker 400 MHz spectrometer.

Example 1: Combinatorial Salt Screen

A salt screen was performed using six solvents (IPA, THF, acetone, acetonitrile, EtOH and EtOAc) and twenty-eight pharmaceutically acceptable acids (HCl, HBr, $H_3PO_4$, $H_2SO_4$, $CH_3SO_3H$, pTSA, BSA, naphthalene sulfonic acid, ethane sulfonic acid, methane sulfonic acid, adipic acid, ethane disulfonic acid, maleic acid, benzoic acid, L-malic acid, citric acid, L-lactic acid, hippuric acid, L-pyroglutamic acid, succinic acid, L-tartaric acid, formic acid, fumaric acid, glutaric acid, L-ascorbic acid, sorbic acid, benzoic acid, and malonic acid). A 96-well plate was charged with 200 µL of a 20 mg/mL solution of compound (I) in MeOH in each well. The solvent was then evaporated under a flow of nitrogen, leaving approximately 4 mg of the starting material in each well. The primary solvent of interest was then added to each well (500 µL). The plates were heated to 50° C. and stirred magnetically for 10 min to ensure complete dissolution of A. Each well was then charged with the designated counterion solution at a volume corresponding to 1.05 equivalents of each acid and allowed to equilibrate at temperature for 10 min. The plates were then cooled at 20° C./h to 25° C., at which point the master plate was daughtered by transferring 200 µL from each well into an evaporation plate. The plates were then cooled to ambient temperature, stored overnight at 5° C. and checked for the presence of solids. The solvent from the master plates was then removed by wicking with sorbent paper. The master and evaporation plates were then dried under nitrogen overnight. Wells that contained solid material were then scored and ranked for birefringence, unique Raman spectrum and threshold solubility. Suitable solvent and counterion combinations were then reevaluated for salt formation with A at an increased scale.

Example 2: Intermediate Scale Salt Formation

Approximately 40 mg of compound (I), was weighed into an 8 mL vial containing a magnetic stir bar. To the vial, primary solvent was added to ensure dissolution at elevated temperature. Following dissolution, 1.05 equivalents of acid was added dropwise as a 0.125, 0.25 or 0.5 M solution. All mixtures were allowed to stir at elevated temperature for 15 min, followed by cooling to room temperature at a rate of 10° C./h and stirring overnight. Samples that did not exhibit precipitation after cooling were scratched with a spatula to induce nucleation and stored in a freezer at −10 to −20° C. The vials were inspected for crystal growth after 1 h. Samples from conditions that afforded solids were centrifuged, filtered or evaporated under nitrogen. All other samples were allowed to equilibrate at −20° C. for 72 h. Vials that did not show precipitation were then dried under nitrogen. The resulting solids were then slurried with IPA for 5 d. From these experiments, only amorphous solids were identified for all counterions except for the fumaric acid salt. Unique polymorphic forms of the fumarate salt of compound (I) are described below.

Preparation of Crystalline Salts of Compound (I)

Example 3: Preparation of Form A of 1:1 Compound (I) Fumarate

Compound (I) (42 mg, 0.078 mmol) was dissolved into acetonitrile (0.5 mL) and heated to 50° C. Fumaric acid (0.33 mL of 0.25M solution in IPA) was added and the mixture stirred for 15 min. The precipitate was filtered and determined to be amorphous due to lack of observable birefringence. The amorphous solid was then slurried with IPA (0.5 mL) for 5 d. The solid obtained from the slurry showed birefringence and was further characterized as an IPA solvate by XRPD, DSC, $^1H$ NMR and TGA and denoted fumarate form A.

TABLE 1

| XRPD of Fumarate Form A | |
|---|---|
| 2θ angle | Rel. Int. (%) |
| 8.17 | 43% |
| 9.69 | 100% |
| 10.69 | 33% |
| 11.51 | 30% |
| 13.63 | 25% |
| 14.89 | 36% |
| 16.73 | 61% |
| 18.09 | 27% |
| 18.83 | 23% |

TABLE 1-continued

| XRPD of Fumarate Form A | |
|---|---|
| 2θ angle | Rel. Int. (%) |
| 20.05 | 50% |
| 23.49 | 34% |
| 24.45 | 26% |

Example 4: Preparation of Form B of 1:1 Compound (I) Fumarate

Desolvation of fumarate form A by vacuum drying at 60° C. for 2 d resulted in a crystalline material with a DSC thermogram and XRPD designated as form B. Form B can also be prepared directly by dissolving the amorphous monofumarate salt in EtOAc and seeding with form B crystals. Gravimetric moisture sorption indicates that the salt form is hygroscopic and forms a tetrahydrate at 90% RH.

TABLE 2

| XRPD of Fumarate Form B | |
|---|---|
| 2θ angle | Rel. Int. (%) |
| 5.51 | 39.5 |
| 5.91 | 38.7 |
| 11.91 | 100.0 |
| 14.93 | 83.5 |
| 16.71 | 40.2 |
| 17.35 | 40.4 |
| 18.73 | 42.8 |
| 21.53 | 41.0 |
| 23.41 | 43.3 |

Example 5: Preparation of Form C of 1:1 Compound (I) Fumarate

A third fumarate polymorph can be obtained by dissolution of amorphous fumarate salt into THF and seeding with fumarate form B crystals. The solvent was slowly evaporated to a white solid which exhibited a XRPD pattern and Raman spectrum different from form B and was designated as fumarate form C.

TABLE 3

| XRPD of Fumarate Form C | |
|---|---|
| 2θ angle | Rel. Int. (%) |
| 9.71 | 68.1 |
| 9.83 | 70.2 |
| 11.71 | 59.5 |
| 15.05 | 60.1 |
| 16.83 | 88.7 |
| 16.87 | 84.7 |
| 19.93 | 100.0 |
| 23.45 | 70.7 |
| 23.65 | 69.6 |

Example 6: Preparation of Form D of 1:1 Compound (I) Fumarate

Slurrying fumarate form C with acetonitrile for 10 d at rt resulted in transition to a new crystal form, denoted form D, which showed a distinct Raman Spectrum and XRPD pattern. The phase transition by DSC was much higher than the other forms and shows the highest stability of the four polymorphs identified. Form D can be directly prepared as follows: A 250-mL three neck RBF equipped with a stir bar was charged with compound (I) (6.01 g, 11 mmol) and fumaric acid (1.41 g, 12 mmol). Acetone (50 mL) was added and the slurry was heated to 50° C. until the solution became clear. Precipitation was observed after 10 min, and stirring was continued for an additional 30 min. MTBE (25 mL) was added and the solution was cooled to rt and stirred overnight. The solids were filtered and dried under vacuum at 60° C. for 2 d to give the title compound (I) as a white solid (6.65 g, 91%).

1H NMR (400 MHz, CD$_3$OD) δ 8.00 (d, J=8.4 Hz, 1H), 7.68 (d, J=8.0 Hz, 2H), 7.50-7.45 (m, 5H), 7.03 (d, J=8.1 Hz, 1H), 6.83 (d, J=8.4 Hz, 1H), 6.73 (s, 2H), 6.60 (dd, J=8.4, 2.5 Hz, 1H), 5.58 (s, 1H), 4.00 (s, 2H), 3.82-3.78 (m, 2H), 3.36 (t, J=8.4 Hz, 1H), 3.26 (s, 3H), 3.13-3.10 (m, 2H), 2.34 (t, J=11.4 Hz, 2H), 2.25-2.16 (m, 2H), 1.01 (d, J=6.0 Hz, 6H).

TABLE 4

| XRPD of Form D | |
|---|---|
| 2θ angle | Rel. Int. (%) |
| 9.59 | 97.3 |
| 11.69 | 39.2 |
| 12.03 | 53.4 |
| 12.83 | 100.0 |
| 15.95 | 92.6 |
| 16.55 | 47.2 |
| 16.93 | 73.3 |
| 18.13 | 47.8 |
| 19.23 | 59.0 |
| 19.81 | 55.4 |
| 20.67 | 59.1 |
| 20.79 | 61.9 |
| 21.23 | 71.5 |
| 21.49 | 66.6 |
| 21.97 | 97.2 |
| 22.53 | 42.1 |
| 23.97 | 53.9 |
| 24.03 | 46.2 |
| 26.03 | 32.5 |
| 29.75 | 41.6 |

The fumaric acid salt can be generated as form D under various conditions. The crystal form can be generated through seeding with crystals of form B or D as shown in Table 5. The salt can be crystallized directly by dissolving the parent compound (I) in polar solvents such as ethyl acetate, acetone or ethanol and delivering fumaric acid in polar solvents such as methanol, ethanol, THF and isopropanol, as shown in Table 6. Yields are generally improved when an antisolvent, such as MTBE, is added. Conditions that do not give form D include when the compound (I) is dissolved into less polar solvents such as acetonitrile, 2-methyltetrahydrofuran and methylisobutyl ketone. Also, addition of hexane as an antisolvent does not promote crystal form D.

The preferred Form D can also be generated by dissolving compound (I) into an appropriate solvent, such as methanol, ethanol, THF or acetone and delivering fumaric acid directly as a solid, as seen in Table 7. Yields are improved when an antisolvent such as MTBE or IBAc is added. Form D is not formed by this method when the primary solvent is less polar, as is the case with ethyl acetate and MTBE.

A 2:1 compound (I)/fumaric acid crystalline salt could not be generated. Two equivalents of compound (I) was dissolved into a primary solvent such as EtOAc, EtOH, THF, IPA and one equivalent of fumaric acid was added as a solid, or in a solution with IPA or EtOH. The resultant solutions were heated to 50° C. for 30 min and cooled to rt. MTBE was added and the mixture was slurried for 24 h. Characterization of both the solid and filtrate by $^1$H NMR revealed only 1:1 compound (I)/fumarate salt was obtained.

TABLE 5

Crystallization of fumarate salt with seeding

| Primary Solvent | Delivery Solvent | Equivalents | Temp (° C.) | Seed addition | Yield (%) | Form |
|---|---|---|---|---|---|---|
| EtOAc | EtOH | 1.05 | 50 | B | 77 | D |
| EtOAc | EtOH | 1.05 | 50 | D | 67 | D |

TABLE 6

Crystallization of fumarate salt

| Primary Solvent | Delivery Solvent | Equivalents | Temp (° C.) | Antisolvent | Yield (%) | Form |
|---|---|---|---|---|---|---|
| EtOAc | MeOH | 1.05 | 50 | MTBE | 54 | D |
| EtOAc | EtOH | 1.05 | 50 | MTBE | 51 | D |
| EtOAc | THF | 1.05 | 50 | MTBE | 53 | D |
| EtOAc | IPA | 1.05 | 50 | MTBE | 50 | D |
| EtOAc | THF | 1.05 | 50 | Hexane | — | — |
| 2-MeTHF | MeOH | 1.05 | 50 | MTBE | — | — |
| 2-MeTHF | EtOH | 1.05 | 50 | MTBE | — | — |
| 2-MeTHF | THF | 1.05 | 50 | MTBE | — | — |
| Acetone | MeOH | 1.05 | 50 | MTBE | 75 | D |
| Acetone | EtOH | 1.05 | 50 | No | 40 | D |
| Acetone | THF | 1.05 | 50 | MTBE | 72 | D |
| Acetone | THF | 1.05 | 50 | Hexane | — | — |
| MIBK | THF | 1.05 | 50 | MTBE | — | — |
| EtOH | THF | 1.05 | 50 | MTBE | 69 | D |
| EtOH | THF | 1.05 | 50 | Hexane | — | — |
| THF | THF | 1.05 | 50 | Hexane | — | — |

TABLE 7

Crystallization with fumaric acid added as solid

| Primary Solvent | Equivalents | Temp (° C.) | Antisolvent | Yield (%) | Form |
|---|---|---|---|---|---|
| MeOH | 1.01 | 50 | No | 43 | D |
| EtOH | 1.14 | 50 | No | 61 | D |
| EtOH | 1.05 | 50 | MTBE | 74 | D |
| EtOH | 1.05 | 50 | IBAc | 74 | D |
| THF | 1.01 | 50 | MTBE | 64 | D |
| Acetone | 0.99 | 50 | No | 53 | D |
| Acetone | 1.05 | 50 | MTBE | 82 | D |
| Acetone | 1.05 | 50 | IBAc | 81 | D |
| EtOAc | 1.01 | 50 | No | — | — |
| MTBE | 1.01 | 50 | No | — | — |

Rescoring of the Combinatorial Salt Screen Results

From the initial combinatorial process, only the fumarate salt was identified as crystalline. The results from the high throughput screen were reevaluated and new scores were generated that were independent of the solvent for each counterion. This rescoring proceeded for the different salts by combining the previous scores (visual inspection of solid formation, birefringence, uniqueness by Raman spectrum and threshold solubility) over all the solvents and summing them up for both the master and evaporation plates.

The two highest rescored acids, maleic and methane sulfonic acid, were further evaluated under additional solvent and antisolvent conditions. Salts obtained from methane sulfonic acid exhibited hygroscopicity. However, a crystalline salt with maleic acid was identified. The preparation and characterization of a maleate salt of compound A is described below.

Example 7: Preparation of Form A of 1:1 Compound (I) Maleate

A 250-mL three neck round bottom flask equipped with a stir bar was charged with compound (I) (4.96 g, 9.3 mmol). Acetone (55 mL) was added and heated to 50° C. Maleic acid (20 mL of 0.5 M solution in acetone) was added resulting in a clear solution which became turbid after 1 min. The solution was cooled to rt and stirred for 24 h as a thick slurry. The solids were filtered, washed with MTBE and dried for 30 h at 60° C. under vacuum to give a white solid (5.52 g, 91%). The salt was characterized as a crystalline by XRPD and denoted form A.

$^1$H NMR (CD$_3$OD) δ: 8.04 (d, J=8.5 Hz, 1H), 7.77 (d, J=8.0 Hz, 2H), 7.45-7.61 (m, 5H), 7.07 (d, J=8.8 Hz, 1H), 6.84 (d, J=8.5 Hz, 1H), 6.62 (dd, J=8.5, 2.5 Hz, 1H), 6.27 (s, 2H), 5.59 (d, J=2.5 Hz, 1H), 4.30 (s, 2H), 3.86-3.82 (m, 2H), 3.34-3.43 (m, 2H), 3.27 (s, 3H), 2.74-2.68 (m, 2H), 2.32-2.10 (m, 2H), 1.23 (d, J=6.3 Hz, 6H).

TABLE 8

XRPD of Maleate Form A

| 2θ angle | rel. intensity |
|---|---|
| 5.45 | 28.2 |
| 5.75 | 54.4 |
| 10.83 | 70.9 |
| 11.49 | 111.9 |
| 12.37 | 79.3 |
| 12.59 | 103.2 |
| 14.05 | 38.1 |
| 14.91 | 96.1 |
| 15.07 | 100.0 |
| 16.73 | 29.6 |
| 17.05 | 75.9 |
| 17.83 | 20.6 |
| 18.55 | 51.7 |
| 19.51 | 34.8 |
| 19.91 | 30.7 |
| 21.89 | 25.9 |
| 22.15 | 34.6 |
| 23.03 | 39.4 |
| 23.31 | 45.3 |
| 23.51 | 56.1 |
| 23.89 | 33.3 |
| 26.09 | 60.3 |

Maleate form A can be generated from a polar solvent, such as EtOH, acetone, isopropyl acetate, ethyl acetate, isopropanol or THF with or without addition of a non-polar antisolvent, such as MTBE. A 2:1 compound (I)/maleic acid crystalline salt could not be generated.

Preparation of Amorphous Salts of Compound (I)

Example 8: Preparation of HCl Salt of Compound (I)

Compound (I) (6.7 g, 12.5 mmol) was dissolved into THF (25 mL) and 1M HCl in ether (13.8 mL, 13.8 mmol) was added at rt and the solution diluted with ether (200 mL). The mixture was stored at rt for 1 h, and the resulting solid was filtered. The solid forms a gel upon standing and was dissolved into water (100 mL) and freeze dried to a yellow powder (5.8 g, 81%).

$^1$H NMR (400 MHz, CD$_3$OD) δ 7.75 (d, J=8.4 Hz, 1H), 7.57 (d, J=8.0 Hz, 2H), 7.46 (d, J=8.0 Hz, 2H), 7.42 (s, 1H), 7.35 (d, J=16.8 Hz, 1H), 7.30 (d, J=16.4 Hz, 1H), 6.82 (d, J=9.2 Hz, 1H), 6.80 (d, J=8.8 Hz, 1H), 6.51 (d, J=8.4 Hz, 1H), 5.19 (s, 1H), 4.28 (s, 2H), 3.92-3.80 (m, 2H), 3.40-3.30 (m, 2H), 3.27 (t, J=8.4 Hz, 1H), 3.15 (s, 3H), 2.70 (t, J=11.4 Hz, 2H), 2.15-2.05 (m, 2H), 1.18 (d, J=6.0 Hz, 6H).

Example 9: Preparation of Phosphate Salt of Compound (I)

Compound (I) (148 mg, 0.27 mmol) was dissolved into EtOAc (0.5 mL) and 0.5M phosphoric acid in EtOAc (0.58 mL, 0.28 mmol) was added at 50° C. and the solution was stirred for 15 min and cooled to rt. The solids were filtered and dried for 4 d at 60° C. to give the title compound (I)s a white solid (149 mg, 85%).

$^1$H NMR (CD$_3$OD) δ 8.00 (d, J=8.5 Hz, 1H), 7.72 (d, J=8.2 Hz, 2H), 7.49-7.58 (m, 5H), 7.04 (d, J=8.0 Hz, 1H), 6.84 (d, J=8.5 Hz, 1H), 6.61 (dd, J=8.5, 2.5 Hz, 1H), 5.58 (d, J=2.5 Hz, 1H), 4.21 (s, 2H), 3.97-3.89 (m, 2H), 3.34-3.39 (m, 1H), 3.26 (s, 3H), 2.55 (t, J=11.8 Hz, 2H), 2.16-2.26 (m, 2H), 1.19 (d, J=6.0 Hz, 6H).

Solubility Test and Pharmacokinetic Analyses

Methods:

A single oral dose in solution and as powder in capsule of the HCl salt of (I), fumarate form D and maleate form A were administered to female Sprague-Dawley rats at 5 mg/kg. Blood samples were collected in the presence of lithium heparin, and were centrifuged to generate plasma. The plasma was then analyzed for compound (I) plasma levels by LC/MS.

Preparation of Test Article for Capsule Dosing in Rats:

All animals involved in the dosing schedule were weighed and assigned numbers. All capsules (Size 9 porcine hard gelatin capsules, Torpac) corresponding with each animal to be dosed were carefully numbered with a fine tip Sharpie. A small plastic weighing dish was placed on the scale, with one capsule lid placed on the dish and the base of the capsule loader with the other part of the capsule was loaded in the reservoir. The balance was tared. A funnel was placed on top of the capsule loading apparatus and the total mass was carefully noted. A piece of 4"×4" wax paper was folded in half creating a crease down the median. A small amount of finely ground compound (Ground the compound if required using mortar and pestle) was deposited in the crease of the wax paper and refolded. The folded wax paper was gently angled over the capsule loader funnel apparatus. A fine scapula was used to tease an amount of compound powder out of the crease onto the funnel allowing it to trickle into the loading bay and ultimately the capsule. The difference in mass from the total mass was noted. The capsule loading funnel was removed and the balance door closed to ascertain the absolute weight of compound inside the capsule. The funnel was returned to the capsule loading apparatus and loading continued until the desired amount of drug was inside the capsule. Note: When adding minute quantities to the capsule, simply brushed fine powered drug that settled on the funnel into the loading column. The funnel was removed and the weight was recorded. Calculated the amount of actual drug by multiplying weighed material by the bioequivalence ratio. The amount of actual drug was recorded. The capsule lid on the weighing dish was used to close the capsule tightly until it clicked into place.

All animals (n=3/group) were dosed orally in a volume of 5 mL/kg. Following dosing, each rat was bled at each of the designated time points. For control animals, blood was collected by the same procedure. Blood was collected from the lateral saphenous vein. Blood aliquots (~50 µL) were collected in tubes coated with lithium heparin, mixed gently, then kept on ice and centrifuged at 2,500×g for 15 minutes at RT, within 1 hour of collection. The plasma layer was collected, kept on ice and finally maintained frozen at −80° C. until further processing.

Bioanalytical Methods

Bioanalytical quantitation using HPLC/tandem quadruple mass spectrometry (HPLC-MS) was performed. Plasma concentrations and $T_{1/2}$ were calculated and reported.

Plasma Assay:

A 5 mg/mL standard solution in DMSO was diluted 100 fold and subsequently serial diluted in 50% DMSO. Aliquots (2 µL) of the serial dilutions were mixed with 18 µL of control plasma (20 µL total) for use as a standard curve. Plasma samples (20 µL) and standard samples were then diluted 5× with ice cold acetonitrile containing 100 ng/mL verapamil as internal standard (80% (v/v) acetonitrile). Acetonitrile precipitated samples and standards were filtered through 0.22 µm membranes in a 96-well format. Filtrates were then diluted with water to 30% acetonitrile.

Dose Assay:

Dosing solution (100 µL) was diluted with DMSO (900 µL) to ensure sample homogeneity. Dilution of the resulting solution into 30% acetonitrile (containing internal standard) was then performed in triplicate to bring the nominal concentration to less than 500 ng/mL, appropriate for LC-MS analysis. Serial dilution from a 5 mg/mL DMSO stock, into 30% acetonitrile (containing internal standard) provided a suitable standard curve. Samples and standards (10 µL) were injected into the LC-MS system, as described below. Concentrations of dose solutions were reported in mg/mL.

LC-MS Analysis:

LC: 10 µL of each sample and standard were injected onto a Waters Acquity CSH 1.7 µm 2.1×100 mm column at 0.6 mL/min by an Acquity UPLC. The C18 column was equilibrated at 10% acetonitrile. Compounds were eluted with a gradient to 99% acetonitrile. All mobile phases contained 0.1% (v/v) formic acid.

Chromatographic Elution:

| t (min) | % B |
| --- | --- |
| 0 | 5 |
| 0.75 | 5 |
| 1 | 20 |
| 4.5 | 99.9 |
| 5 | 99.9 |
| 5.4 | 5 |
| 6 | 5 |

MS: Column eluent was analyzed by electrospray ionization into a tandem quadrupole mass spec system (Waters Xevo TQ). Eluent composition was analyzed for three ion-pairs specific for the internal standard and three ion-pairs specific for the analyte.

Pharmacokinetic Analyses

Experimental samples were compared with standard curve samples to determine compound concentrations. Average compound concentrations (in µg/mL +/− standard deviation) were reported for each time-point. Limit of Detection (LLOQ) was reported as the lowest standard curve sample demonstrating a deviation of less than 20% of nominal concentration. PK analysis was performed by the Excel plugin PKfit; $C_{max}$ were determined as the maximum average concentration observed at a given time point; the area under the curve (AUC) was reported for $t_0$ to $t_{last}$ hours. Plasma half-lives were reported when a minimum of 3 terminal time-points demonstrated first order elimination with an $r^2 > 0.8$.

As shown in Table 9, crystalline salts of compound (I) were shown to be less soluble in deionized water compared to the amorphous phosphate and HCl salts. In many reported cases, the increased solubility of the amorphous salts results in an increase in plasma concentrations relative to a more stable crystalline form (Hancock and Parks (2000) Pharm. Res. 17: 397-404; Pudipeddi and Serajuddin (2005) J. Pharm. Sci. 94: 929-39). However, when the plasma concentration-time profiles and pharmacokinetic parameters of amorphous and crystalline salts were compared following oral dosing as powder in capsule (PIC) to female Sprague-Dawley rats, the difference in pharmacokinetic parameters was minimal (Table 10).

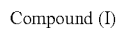
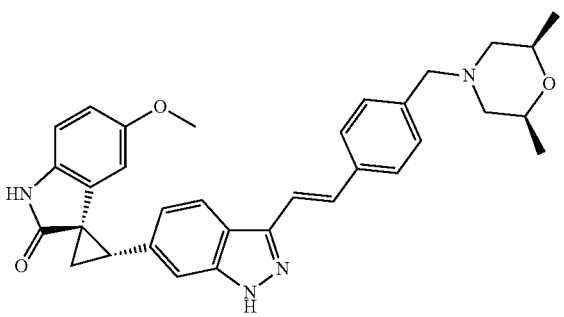

wherein the molar ratio between compound (I) and fumaric acid is 1:1, wherein the cancer is selected from the group consisting of lung cancer, breast cancer and colon cancer.

2. The method of claim 1, wherein the fumarate salt is crystalline.

TABLE 9

Characterization summary of compound (I) Salts

| Counterion | XRPD | Compound (I):acid ratio | DSC (° C.) | TGA Loss (wt %) | Gravimetric Moisture Sorption | Solubility in DI water (µg/mL) |
| --- | --- | --- | --- | --- | --- | --- |
| Fumarate | A | 1.0:0.9 | 112, 158 | 7.2 (45-160° C.) | | |
| Fumarate | B | 1.0:1.0 | 58, 162 | 2.6 (40-120° C.) | 3.7 wt % 60% RH 10.5 wt % 90% RH | |
| Fumarate | C | 1.0:1.1 | 62, 156 | 2.6 (30-100° C.) | | 625 |
| Fumarate | D | 1.0:1.0 | 219 | 0.9 (30-100° C.) | 2.1 wt % 60% RH 4.0 wt % 90% RH | 170 |
| Maleate | A | 1.0:0.95 | 219 | No loss observed until melt | 1.3 wt %, 60% RH 2.2 wt %, 90% RH | |
| Phosphate | Amorphous | 1.0:1.1 | 83, 179 | 1.9 | 6.1 wt % 60% RH 10.9 wt % 90% RH | $\geq 1 \times 10^5$ |
| HCl | Amorphous | | | 2.3 (30-150° C.) | | $\geq 1 \times 10^5$ |

TABLE 10

Pharmacokinetic Parameters after PO Administration of (I) Salts, Powder in Capsule, to Sprague-Dawley Rats

| Salt form | HCl | Fumarate (form D) | Maleate (form A) |
| --- | --- | --- | --- |
| Oral Dose (mg/kg) | 5.0 | 5.0 | 5.0 |
| Cmax (ng/mL) | 250 | 270 | 200 |
| $AUC_{9-tlast}$ (ng.h/mL) | 2400 | 2780 | 1500 |

What is claimed is:

1. A method of treating a subject with cancer, comprising administering to the subject an effective amount of a fumarate salt of compound (I) represented by the following structural formula:

3. The method of claim 1, wherein the fumarate salt is in a single crystalline form.

4. The method of claim 2, wherein at least 99% by weight of the fumarate salt is crystalline.

5. The method of claim 3, wherein at least 99% by weight of the fumarate salt is in a single crystalline form.

6. The method of claim 1, wherein the fumarate salt is single crystalline form A, characterized by an X-ray powder diffraction pattern which comprises peaks at 8.2°, 9.7°, 16.7°, and 20.1°±0.2 in 2θ.

7. The method of claim 1, wherein the fumarate salt is single crystalline form A, characterized by an X-ray powder diffraction pattern which comprises peaks at 8.2°, 9.7°, 10.7°, 11.5°, 14.9°, 16.7°, 20.1°, and 23.5°±0.2 in 2θ.

8. The method of claim 1, wherein the fumarate salt is single crystalline form B, characterized by an X-ray powder diffraction pattern which comprises peaks at 11.9°, 14.9°, 18.7°, and 21.5°±0.2 in 2θ.

9. The method of claim 1, wherein the fumarate salt is single crystalline form B, characterized by an X-ray powder diffraction pattern which comprises peaks at 5.5°, 5.9°, 11.9°, 14.9°, 16.7°, 17.4°, 18.7°, 21.5°, and 23.4°±0.2 in 2θ.

10. The method of claim 1, wherein the fumarate salt is single crystalline form C, characterized by an X-ray powder diffraction pattern which comprises peaks at 9.8°, 16.8°, 16.9°, 19.9°, and 23.5°±0.2 in 2θ.

11. The method of claim 1, wherein the fumarate salt is single crystalline form C, characterized by an X-ray powder diffraction pattern which comprises peaks at 9.7°, 9.8°, 11.7°, 15.1°, 16.8°, 16.9°, 19.9°, 23.5°, and 23.7°±0.2 in 2θ.

12. The method of claim 1, wherein the fumarate salt is single crystalline form D, characterized by an X-ray powder diffraction pattern which comprises peaks at 9.6°, 12.8°, 16.0°, and 22.0°±0.2 in 2θ.

13. The method of claim 1, wherein the fumarate salt is single crystalline form D, characterized by an X-ray powder diffraction pattern which comprises peaks at 9.6°, 12.8°, 16.0°, 16.9°, 21.2°, and 22.0°±0.2 in 2θ.

14. The method of claim 1, wherein the fumarate salt is single crystalline form D, characterized by an X-ray powder diffraction pattern which comprises peaks at 9.6°, 12.8°, 16.0°, 16.9°, 20.8°, 21.2°, 21.5°, and 22.0°±0.2 in 2θ.

15. The method of claim 1, wherein the fumarate salt is single crystalline form D, characterized by an X-ray powder diffraction pattern which comprises peaks at 9.6°, 11.7°, 12.0°, 12.8°, 16.0°, 16.6°, 16.9°, 18.1°, 19.2°, 19.8°, 20.7°, 20.8°, 21.2°, 21.5°, 22.0°, 22.5°, 24.0°, 26.0°, and 29.8°±0.2 in 2θ.

16. The method of claim 6, wherein the fumarate salt is single crystalline form A, characterized by differential scanning calorimeter (DSC) peak phase transition temperatures of 112° C. and 158° C.

17. The method of claim 8, wherein the fumarate salt is single crystalline form B, characterized by differential scanning calorimeter (DSC) peak phase transition temperatures of 58° C. and 162° C.

18. The method of claim 10, wherein the fumarate salt is single crystalline form C, characterized by differential scanning calorimeter (DSC) peak phase transition temperatures of 62° C. and 156° C.

19. The method of claim 12, wherein the fumarate salt is single crystalline form D, characterized by differential scanning calorimeter (DSC) peak phase transition temperature of 219° C.

20. The method of claim 1, wherein the cancer is breast cancer.

21. The method of claim 20, wherein the cancer is basal sub-type breast cancer or a luminal B sub-type breast cancer.

22. The method of claim 20, wherein the cancer is basal sub-type breast cancer that is ER, HER2 and PR negative breast cancer.

* * * * *